(12) United States Patent
Champagne et al.

(10) Patent No.: US 11,259,849 B2
(45) Date of Patent: Mar. 1, 2022

(54) FULL WRIST FUSION DEVICE

(71) Applicant: ExsoMed Holding Company, LLC, Scottsdale, AZ (US)

(72) Inventors: Lloyd P. Champagne, Phoenix, AZ (US); Jozef Zoldos, Phoenix, AZ (US)

(73) Assignee: ExsoMed Corporation, Aliso Viejo, CA (US)

( * ) Notice: Subject to any disclaimer, the term of this patent is extended or adjusted under 35 U.S.C. 154(b) by 0 days.

(21) Appl. No.: 14/503,228

(22) Filed: Sep. 30, 2014

(65) Prior Publication Data
US 2015/0094722 A1    Apr. 2, 2015

Related U.S. Application Data

(60) Provisional application No. 61/885,748, filed on Oct. 2, 2013.

(51) Int. Cl.
*A61B 17/72* (2006.01)
*A61B 17/80* (2006.01)

(52) U.S. Cl.
CPC ...... *A61B 17/7291* (2013.01); *A61B 17/8061* (2013.01)

(58) Field of Classification Search
CPC . A61F 2/4261; A61F 2002/4264–4297; A61B 17/7291
See application file for complete search history.

(56) References Cited

U.S. PATENT DOCUMENTS

| 1,741,279 A | 12/1929 | Bowman |
| 2,037,586 A | 4/1936 | Olson |
| 2,210,455 A | 8/1940 | Hosking |
| 2,217,951 A | 10/1940 | Hosking |
| 2,229,892 A | 1/1941 | Hosking |
| 2,242,003 A | 5/1941 | Lorenzo |
| 3,078,900 A | 2/1963 | Walker |
| 3,275,055 A | 9/1966 | Gutshall |
| 3,397,699 A | 8/1968 | Kohl |
| 3,717,146 A | 2/1973 | Halloran |
| 4,016,874 A | 4/1977 | Maffei |

(Continued)

FOREIGN PATENT DOCUMENTS

| CH | 643131 | 5/1984 |
| CH | 646858 | 12/1984 |

(Continued)

OTHER PUBLICATIONS

PCT; International Search Report and Written Opinion dated Sep. 17, 2010 in Application No. PCT/US2009/046662.

(Continued)

*Primary Examiner* — Nicholas J Plionis
(74) *Attorney, Agent, or Firm* — Knobbe, Martens, Olson & Bear, LLP

(57) ABSTRACT

Disclosed is a device for total wrist fusion that includes (a) a first section, which is preferably a plate, that is positioned under the skin on top of the forearm, wrist and potentially part of the hand and connected to one or more of the radius or carpal bones, (b) a second section, which is preferably in the shape of an awl and is received in the cannula of the third metacarpal bone. Optionally, an anti-rotational third section may be included, which can connect to the top of the third metacarpal bone.

19 Claims, 5 Drawing Sheets

(56) References Cited

U.S. PATENT DOCUMENTS

| | | |
|---|---|---|
| 4,175,555 A | 11/1979 | Herbert |
| 4,350,465 A | 9/1982 | Lovisek |
| 4,380,414 A | 4/1983 | Capuano |
| 4,463,753 A | 8/1984 | Gustilo |
| 4,471,777 A | 9/1984 | McCorkle |
| 4,584,722 A | 4/1986 | Levy et al. |
| 4,608,965 A | 9/1986 | Anspach |
| 4,653,487 A * | 3/1987 | Maale ............... A61B 17/7098 606/62 |
| 4,764,066 A | 8/1988 | Terrell |
| 4,781,191 A | 11/1988 | Thompson |
| 4,812,095 A | 3/1989 | Piacenti |
| 4,820,235 A | 4/1989 | Weber et al. |
| 4,842,463 A | 6/1989 | Landt |
| 4,901,717 A | 2/1990 | Moore et al. |
| 4,909,789 A | 3/1990 | Taguchi et al. |
| 5,061,283 A | 10/1991 | Silvestrini |
| 5,234,299 A | 8/1993 | Giannuzzi |
| 5,312,255 A | 5/1994 | Bauer |
| 5,345,927 A | 9/1994 | Bonutti |
| 5,443,466 A * | 8/1995 | Shah ..................... A61B 17/72 606/323 |
| 5,522,846 A | 6/1996 | Bonutti |
| 5,645,545 A | 7/1997 | Bryant |
| 5,667,510 A | 9/1997 | Combs |
| 5,690,633 A | 11/1997 | Taylor et al. |
| 5,840,078 A | 11/1998 | Yerys |
| 5,853,413 A | 12/1998 | Carter et al. |
| 6,187,007 B1 | 2/2001 | Frigg |
| 6,221,006 B1 | 4/2001 | Dubrul et al. |
| 6,231,319 B1 | 5/2001 | Lida et al. |
| 6,231,413 B1 | 5/2001 | Tsukamoto |
| 6,306,140 B1 | 10/2001 | Siddiqui |
| 6,394,725 B1 | 5/2002 | Dicke |
| 6,475,242 B1 | 11/2002 | Bramlet |
| 6,517,541 B1 | 2/2003 | Sesic |
| 6,592,623 B1 | 7/2003 | Bowlin et al. |
| 6,607,530 B1 | 8/2003 | Carl et al. |
| 6,808,526 B1 | 10/2004 | Magerl et al. |
| 7,037,309 B2 | 5/2006 | Well et al. |
| 7,041,106 B1 | 5/2006 | Carver et al. |
| 7,063,491 B2 | 6/2006 | French |
| 7,334,976 B2 | 2/2008 | Dicke |
| 7,465,135 B2 | 12/2008 | Fritsch |
| 7,507,242 B2 | 3/2009 | Triplett et al. |
| 7,604,659 B2 | 10/2009 | Lee |
| 7,708,738 B2 | 5/2010 | Fourcault et al. |
| 7,766,942 B2 | 8/2010 | Patterson |
| 7,988,724 B2 | 8/2011 | Salahieh et al. |
| 8,011,866 B2 | 9/2011 | Harris |
| 8,157,803 B1 * | 4/2012 | Zirkle, Jr ............. A61B 17/744 606/64 |
| 8,348,575 B2 | 1/2013 | Walther |
| 8,398,687 B2 | 3/2013 | Vasta et al. |
| 8,414,648 B2 | 4/2013 | Reiley |
| 8,419,776 B2 | 4/2013 | Prandi et al. |
| 8,518,042 B2 | 8/2013 | Winsow et al. |
| 8,568,462 B2 | 10/2013 | Sixto et al. |
| 8,597,337 B2 | 12/2013 | Champagne |
| 8,608,783 B2 | 12/2013 | Graham et al. |
| 8,814,918 B2 | 8/2014 | Orbay et al. |
| 8,852,253 B2 | 10/2014 | Mafi |
| 8,864,804 B2 | 10/2014 | Champagne et al. |
| 8,888,429 B2 | 11/2014 | Pamer |
| 8,906,075 B2 | 12/2014 | Conley et al. |
| 9,017,404 B2 | 4/2015 | Champagne et al. |
| 9,046,120 B2 | 6/2015 | Phua |
| 9,086,088 B2 | 7/2015 | Walther |
| 9,175,715 B2 | 11/2015 | Babej |
| 9,265,600 B2 | 2/2016 | Niese |
| 9,480,515 B2 | 11/2016 | Champagne |
| 9,539,084 B2 | 1/2017 | Champagne |
| 10,098,680 B2 | 10/2018 | Champagne |
| 10,441,330 B2 | 10/2019 | Champagne et al. |
| 2001/0049529 A1 | 12/2001 | Cachia et al. |
| 2002/0045897 A1 * | 4/2002 | Dixon ............... A61B 17/1728 606/286 |
| 2002/0055747 A1 | 5/2002 | Cano et al. |
| 2002/0055749 A1 | 5/2002 | Esnouf et al. |
| 2002/0143337 A1 * | 10/2002 | Orbay ............... A61B 17/7208 606/62 |
| 2002/0198527 A1 | 12/2002 | Muckter |
| 2003/0014077 A1 | 1/2003 | Leung |
| 2003/0083661 A1 * | 5/2003 | Orbay ............... A61B 17/8061 606/62 |
| 2003/0130735 A1 | 7/2003 | Rogalski |
| 2004/0193217 A1 | 9/2004 | Lubbers |
| 2004/0210227 A1 | 10/2004 | Trail et al. |
| 2004/0260288 A1 | 12/2004 | Means |
| 2005/0075642 A1 | 4/2005 | Felt et al. |
| 2005/0085824 A1 * | 4/2005 | Castaneda .......... A61B 17/1725 606/98 |
| 2005/0107791 A1 | 5/2005 | Manderson |
| 2005/0143735 A1 | 6/2005 | Kyle |
| 2006/0089647 A1 * | 4/2006 | Culbert ................ A61B 17/68 606/65 |
| 2006/0129153 A1 | 6/2006 | Klaue et al. |
| 2006/0149249 A1 | 7/2006 | Mathoulin et al. |
| 2006/0165506 A1 | 7/2006 | Panasik |
| 2006/0189987 A1 | 8/2006 | Orbay et al. |
| 2006/0195099 A1 | 8/2006 | Bottlang |
| 2006/0271061 A1 | 11/2006 | Beyar |
| 2006/0276790 A1 | 12/2006 | Dawson |
| 2007/0027547 A1 | 2/2007 | Rydell et al. |
| 2007/0135816 A1 | 6/2007 | Kropf et al. |
| 2007/0282342 A1 | 12/2007 | Niederberger et al. |
| 2007/0299449 A1 | 12/2007 | Allinniemi et al. |
| 2008/0183220 A1 | 7/2008 | Glazer |
| 2008/0219801 A1 | 9/2008 | Toenjes |
| 2008/0249547 A1 | 10/2008 | Dunn |
| 2008/0249574 A1 | 10/2008 | McCombs et al. |
| 2009/0062868 A1 | 3/2009 | Casutt |
| 2009/0299369 A1 | 12/2009 | Orbay et al. |
| 2010/0106254 A1 | 4/2010 | Delsignore |
| 2010/0121136 A1 | 5/2010 | Champagne |
| 2010/0130978 A1 * | 5/2010 | Orbay ............... A61B 17/1782 606/62 |
| 2010/0211115 A1 | 8/2010 | Tyber et al. |
| 2010/0278614 A1 | 11/2010 | Bickford |
| 2010/0312286 A1 | 12/2010 | Dell'Oca |
| 2010/0324556 A1 | 12/2010 | Tyber et al. |
| 2011/0009865 A1 | 1/2011 | Orfaly |
| 2011/0130794 A1 | 6/2011 | Vaidya |
| 2012/0083847 A1 | 4/2012 | Heubner et al. |
| 2012/0136398 A1 | 5/2012 | Mobasser |
| 2012/0191140 A1 | 7/2012 | Bonutti |
| 2012/0209270 A1 * | 8/2012 | Segina ............... A61B 17/8061 606/67 |
| 2012/0221104 A1 | 8/2012 | Altman et al. |
| 2012/0253464 A1 | 10/2012 | Hwang et al. |
| 2012/0253465 A1 | 10/2012 | Missos |
| 2013/0012987 A1 | 1/2013 | Klein et al. |
| 2013/0053961 A1 | 2/2013 | Darwin et al. |
| 2013/0060333 A1 | 3/2013 | Gonzalez |
| 2013/0131699 A1 | 5/2013 | Jiang et al. |
| 2013/0138123 A1 | 5/2013 | Stone et al. |
| 2013/0165979 A1 * | 6/2013 | Greenberg ......... A61B 17/8061 606/281 |
| 2013/0190872 A1 | 7/2013 | Makower et al. |
| 2013/0197592 A1 | 8/2013 | Mafi |
| 2013/0245626 A1 | 9/2013 | Lavi et al. |
| 2013/0245700 A1 | 9/2013 | Choinski |
| 2013/0245762 A1 | 9/2013 | Van Kampen et al. |
| 2013/0261662 A1 | 10/2013 | Mayer et al. |
| 2013/0274879 A1 | 10/2013 | Champagne et al. |
| 2013/0282058 A1 | 10/2013 | ElAttrache et al. |
| 2013/0325011 A1 | 12/2013 | Cleveland et al. |
| 2014/0025124 A1 | 1/2014 | Champagne et al. |
| 2014/0067063 A1 | 3/2014 | Bonutti |
| 2014/0257349 A1 | 9/2014 | Sudekum |
| 2014/0276846 A1 | 9/2014 | Mauldin |
| 2014/0336712 A1 | 11/2014 | Stmad et al. |
| 2015/0066060 A1 | 3/2015 | Bojarski |

(56) References Cited

U.S. PATENT DOCUMENTS

| | | |
|---|---|---|
| 2015/0094724 A1 | 4/2015 | Champagne et al. |
| 2015/0094777 A1 | 4/2015 | Champagne et al. |
| 2015/0173737 A1 | 6/2015 | Champagne et al. |
| 2015/0182325 A1 | 7/2015 | Champagne et al. |
| 2016/0030097 A1 | 2/2016 | Mildner |
| 2016/0256290 A1 | 9/2016 | Seavey et al. |
| 2016/0296263 A1 | 10/2016 | Champagne et al. |
| 2016/0296264 A1 | 10/2016 | Champagne et al. |
| 2016/0338748 A1 | 11/2016 | Champagne et al. |
| 2017/0027577 A1 | 2/2017 | Kubiak et al. |
| 2017/0035553 A1 | 2/2017 | Champagne et al. |
| 2017/0049167 A1 | 2/2017 | Champagne et al. |
| 2017/0189090 A1 | 7/2017 | Champagne et al. |
| 2017/0196609 A1 | 7/2017 | Champagne et al. |
| 2017/0325827 A1 | 11/2017 | Champagne et al. |
| 2018/0021124 A1 | 1/2018 | Champagne et al. |
| 2019/0336185 A1 | 11/2019 | Champagne et al. |
| 2020/0214750 A1 | 7/2020 | Champagne et al. |

FOREIGN PATENT DOCUMENTS

| | | |
|---|---|---|
| DE | 2713386 | 11/1978 |
| DE | 102007003645 | 7/2008 |
| DE | 202013101135 | 6/2014 |
| EP | 0597223 | 5/1994 |
| EP | 1378205 | 1/2004 |
| EP | 2606843 | 6/2013 |
| EP | 602013043888.9 | 9/2018 |
| GB | 2007099 | 5/1979 |
| GB | 2181356 | 4/1987 |
| WO | WO199733537 | 9/1997 |
| WO | WO2004093700 | 4/2004 |
| WO | WO2005092226 | 10/2005 |
| WO | WO2006105935 | 12/2006 |
| WO | WO2007081601 | 7/2007 |
| WO | WO2007109140 | 9/2007 |
| WO | WO2008063156 | 5/2008 |
| WO | WO2010151589 | 12/2010 |
| WO | 2012050424 | 4/2012 |
| WO | WO2014011933 | 1/2014 |
| WO | 2014089522 | 6/2014 |
| WO | 2015050900 | 4/2015 |
| WO | WO2015050895 | 9/2015 |
| WO | WO2015050896 | 9/2015 |
| WO | WO2015050898 | 9/2015 |
| WO | WO2015050902 | 9/2015 |
| WO | 2016186847 | 11/2016 |

OTHER PUBLICATIONS

EP; Examination Report dated May 30, 2011 in Application No. EP 09774002.1.
USPTO; Office Action dated Oct. 4, 2011 in U.S. Appl. No. 12/372,712.
USPTO; Office Action dated Mar. 21, 2012 in U.S. Appl. No. 12/480,676.
EP; Examination Report dated May 25, 2012 in Application No. EP 09774002.1.
USPTO; Office Action dated May 29, 2012 in U.S. Appl. No. 12/372,712.
USPTO; Office Action dated Sep. 18, 2012 in U.S. Appl. No. 12/480,676.
USPTO; Office Action dated Mar. 22, 2013 in U.S. Appl. No. 12/372,712.
USPTO; Notice of Allowance dated Jul. 30, 2013 in U.S. Appl. No. 12/372,712.
PCT; International Search Report and Written Opinion dated Sep. 9, 2013 in Application No. PCT/US2013/050155.
USPTO; Office Action dated Sep. 24, 2013 in U.S. Appl. No. 12/480,676.
USPTO; Office Action dated Feb. 18, 2014 in U.S. Appl. No. 13/555,933.
USPTO; Notice of Allowance dated Jun. 25, 2014 in U.S. Appl. No. 13/555,933.
USPTO; Office Action dated Aug. 29, 2014 in U.S. Appl. No. 13/648,019.
PCT; International Search Report and Written Opinion dated Dec. 10, 2014 in Application No. PCT/US2014/058463.
PCT; International Search Report and Written Opinion dated Dec. 12, 2014 in Application No. PCT/US2014/058474.
USPTO; Notice of Allowance dated Dec. 31, 2014 in U.S. Appl. No. 13/648,019.
PCT; International Search Report and Written Opinion dated Jan. 20, 2015 in Application No. PCT/US2014/058448.
PCT; International Search Report and Written Opinion dated Feb. 9, 2015 in Application No. PCT/US2014/058441.
USPTO; Office Action dated Dec. 9, 2015 in U.S. Appl. No. 14/640,657.
USPTO; Office Action dated Oct. 5, 2015 in U.S. Appl. No. 13/940,173.
USPTO; Final Office Action dated May 23, 2016 in U.S. Appl. No. 13/940,173.
USPTO; Notice of Allowance dated Jul. 1, 2016 in U.S. Appl. No. 13/940,173.
USPTO; Notice of Allowance dated Sep. 1, 2016 in U.S. Appl. No. 14/640,657.
USPTO; Non-Final Office Action dated Apr. 10, 2017 in U.S. Appl. No. 14/641,024.
USPTO; Final Office Action dated Jun. 2, 2017 in U.S. Appl. No. 14/503,157.
USPTO; Final Office Action dated Jun. 13, 2017 in U.S. Appl. No. 14/503,119.
USPTO; Non-Final Office Action dated Nov. 4, 2016 in U.S. Appl. No. 14/503,119.
USPTO; Non-Final Office Action dated Jan. 27, 2017 in U.S. Appl. No. 14/503,157.
USPTO; Non-Final Office Action dated Feb. 21, 2018 in U.S. Appl. No. 15/151,252.
USPTO; Non-Final Office Action dated Feb. 27, 2018 in U.S. Appl. No. 14/503,157.
USPTO; Non-Final Office Action dated Mar. 5, 2018 in U.S. Appl. No. 14/993,972.
USPTO; Non-Final Office Action dated Mar. 5, 2018 in U.S. Appl. No. 15/214,412.
PCT; International Search Report and Written Opinion dated Sep. 30, 2014 in Application No. PCT/US2014/058472.
PCT; International Search Report and Written Opinion dated May 4, 2016 in Application No. PCT/US2016/030850.
USPTO; Non-Final Office Action dated Nov. 1, 2017 in U.S. Appl. No. 15/297,698.
USPTO; Non-Final Office Action dated Nov. 28, 2017 in U.S. Appl. No. 15/189,845.
USPTO; Non-Final Office Action dated Nov. 30, 2017 in U.S. Appl. No. 15/189,829.
USPTO; Requirement for Restriction dated Nov. 30, 2017 in U.S. Appl. No. 15/214,412.
USPTO; Non-Final Office Action dated Dec. 8, 2017 in U.S. Appl. No. 15/146,824.
USPTO; Non-Final Office Action dated Dec. 15, 2017 in U.S. Appl. No. 14/984,145.
EP; Examination Report dated Feb. 12, 2016 in Application No. EP 13742332.3.
EP; 2nd Examination Report dated Oct. 11, 2016 in Application No. EP 13742332.3.
EP; Notice of Allowance dated Apr. 12, 2018 in Application No. EP 13742332.3.
USPTO; Notice of Allowance dated Jun. 15, 2018 in U.S. Appl. No. 15/189,845.
USPTO; Final Office Action dated Jun. 26, 2018 in U.S. Appl. No. 14/984,145.
USPTO; Notice of Allowance dated Jul. 11, 2018 in U.S. Appl. No. 15/189,845.
USPTO; Final Office Action dated Jul. 20, 2018 in U.S. Appl. No. 14/993,972.

(56) References Cited

OTHER PUBLICATIONS

USPTO; Final Office Action dated Aug. 8, 2018 in U.S. Appl. No. 15/214,412.
USPTO; Final Office Action dated Aug. 13, 2018 in U.S. Appl. No. 15/151,252.
USPTO; Notice of Allowance dated Sep. 18, 2018 in U.S. Appl. No. 15/151,252.
USPTO; Final Office Action dated Oct. 17, 2018 in U.S. Appl. No. 15/146,824.

* cited by examiner

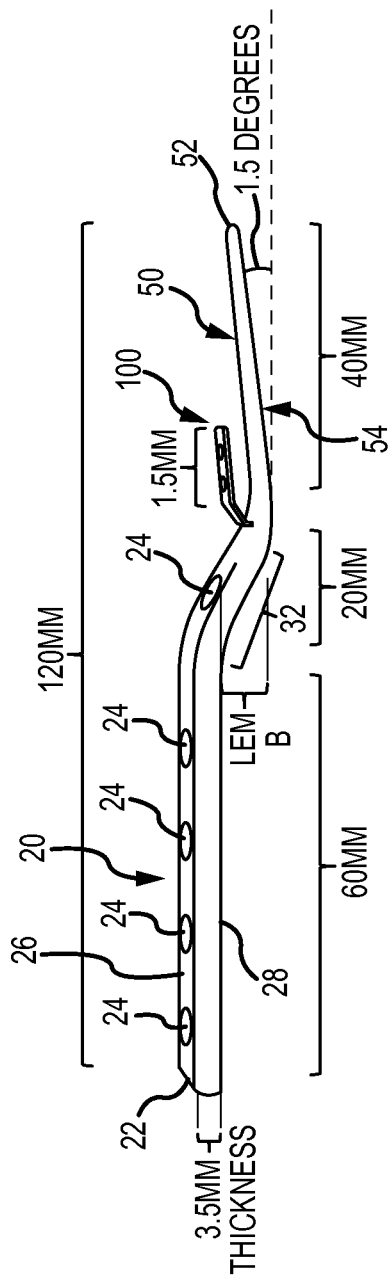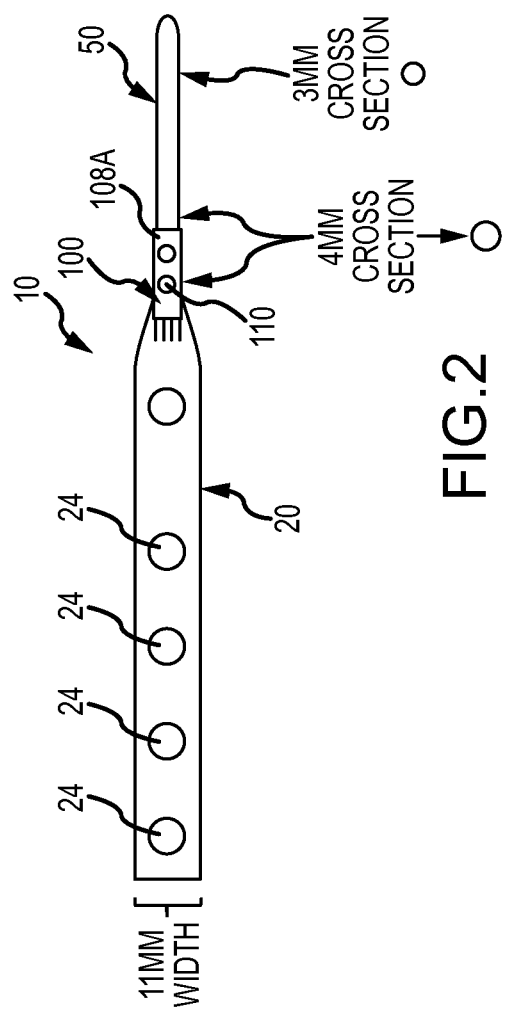

FULL WRIST FUSION DEVICE

FIELD OF THE INVENTION

The present invention is related to a device and method that provides full wrist fusion.

BACKGROUND OF THE INVENTION

Generally, wrist fusion apparatuses are used in patients with post-traumatic or degenerative wrist arthritis, conditions involving significant loss of bone substance, or failed total and partial wrist arthrodesis. Wrist arthrodesis can also be utilized in patients with complex fractures of the wrist, or with rheumatoid arthritis.

It is common for some types of wrist fusion apparatuses to extend from the radius to a metacarpal, particularly the third metacarpal, of the hand. Wrist fusion apparatuses of this variety are typically fastened both to the radius and to the third metacarpal by bone screws, and wrist fusion apparatuses of this type also therefore overlie the carpus area and the bones of the carpus area, which are positioned between the radius and the metacarpal bones. As known to those of skill in the art, bone grafts can be packed between the radius, the carpus area bones, and the metacarpals after such a wrist fusion plate is in place, and the bone grafts typically will bond with the adjacent bones in order to create a fused bone mass at the wrist joint.

Because wrist fusion plate apparatuses and methods require attachment of a portion of the wrist fusion plate to one or more of the metacarpals of the hand, they can cause undesirable disadvantages, such as the development of extensor tendinitis at the prominent distal end of the plate (which may necessitate removal of the plate and a second surgical procedure).

SUMMARY OF THE INVENTION

The present disclosure generally relates to a device for application to a wrist joint for use in an orthopaedic procedure, and, more particularly, to a wrist fusion plate for fusing a wrist joint. The wrist fusion device of the invention may be applicable for correction of bone deformation due to arthritis, rheumatoid arthritis, inflammatory diseases such as rheumatic fever or tuberculosis, genetic disorders of the bone, or for setting a wrist fracture.

Aspects of the present device include a first section, most preferably in the form of a metal bar or plate, that is positioned over the top of the forearm and extends past the wrist to fuse the wrist to the forearm and preferably fuse the bones in the wrist. The device further includes a second section integrally formed with or connected to the first section. The second section preferably narrows to the shape of a spike or awl. In use, an appropriate incision is made, such as lengthwise along the hand, wrist and forearm. The wrist is bent and the second section is pushed under the skin of the hand until it is properly seated inside of the cannula of the third metacarpal bone (the material in the cannula may be loosened first, using any suitable technique or device). One the second section is in place, the wrist is preferably straightened and the first section is placed under the skin across the wrist and onto the top the forearm. The plate is then secured using any suitable technique, such as bone screws that pass through apertures on the plate and into one or more of the radius and/or carpal bones.

A device according to the invention may include an anti-rotational third section. The third section may be connected to or integrally formed with the rest of the device. One aspect of the anti-rotational device could be a plate that extends upward and outward, above the second section, and is secured by one or more fasteners to the top of the third metacarpal bone.

The one or more fasteners may also be received in the part of the second section that is positioned in the cannula of the third metacarpal to provide additional anti-rotational stability. Further, an anti-rotational structure may be provided that includes no third section, but merely one or more fasteners that pass through, and are connected to, the top of the third metacarpal bone and that are also received in the second section.

BRIEF DESCRIPTION OF THE DRAWINGS

FIG. 1 is a perspective, side view of a device according to aspects of the invention.

FIG. 2 is a top view of the device of FIG. 1.

DETAILED DESCRIPTION OF PREFERRED EMBODIMENTS

Turning now to the Figures, where the purpose is to describe preferred embodiments according to the invention and not limit same, FIG. 1 shows a perspective side view of a device 10 according to aspects of the invention. Device 10 has a first section 20 and a second section 50. In one preferred embodiment device 10 has an overall length of between 90 and 150 mm, and is most preferably about 120 mm in length, and is comprised of stainless steel although any suitable material for permanent placement in the body would suffice.

Figure 6:
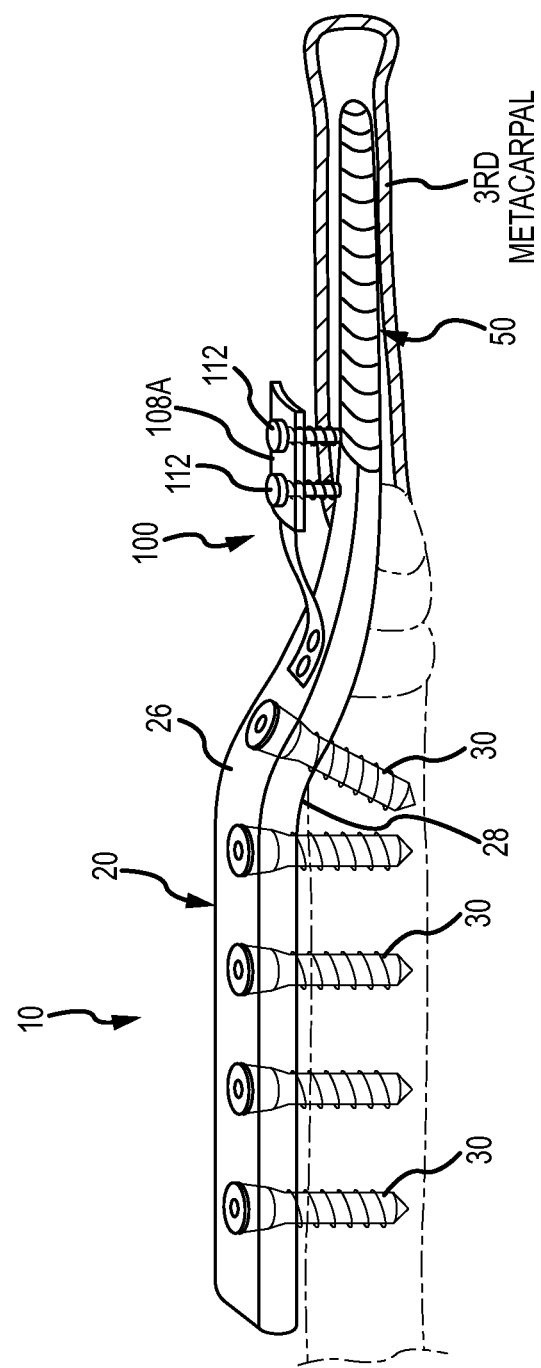
FIG. 6 is the device of FIG. 5 fully connected to a patient's forearm, wrist and hand.
Figure 7:
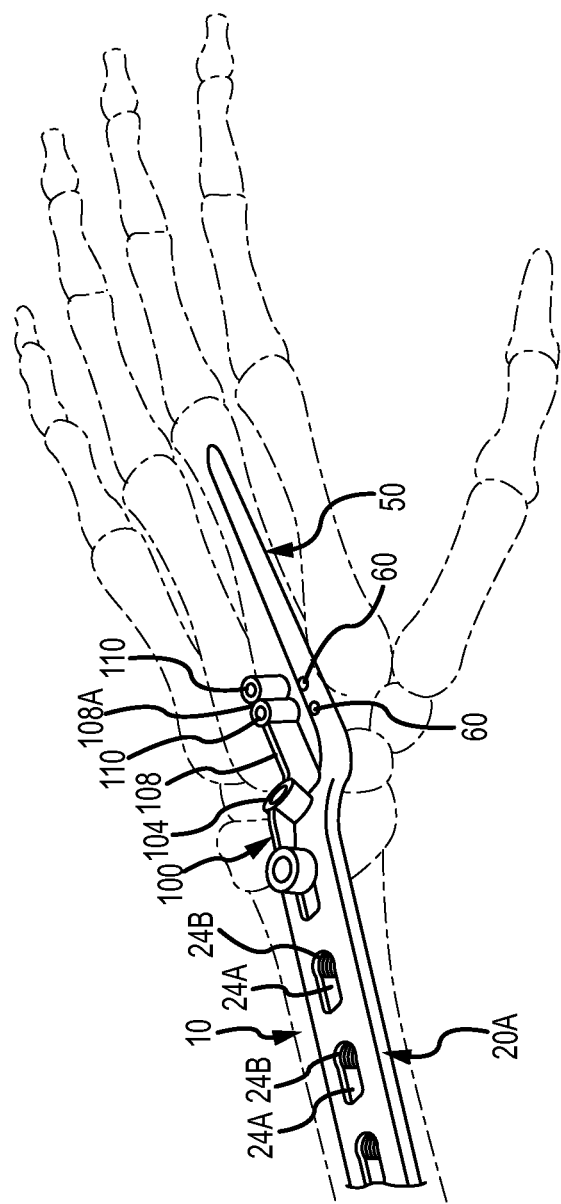
FIG. 7 is another device according to aspects of the invention showing how it is positioned on patient's forearm, wrist and hand.

First section 20 is configured to fit under the skin of the forearm and wrist and connect to the radius bone and one or more carpal bones in the forearm and/or wrist in order to secure section 20. FIGS. 6 and 7 illustrate a device 10 according to the invention fully inserted and attached.

Figure 5:
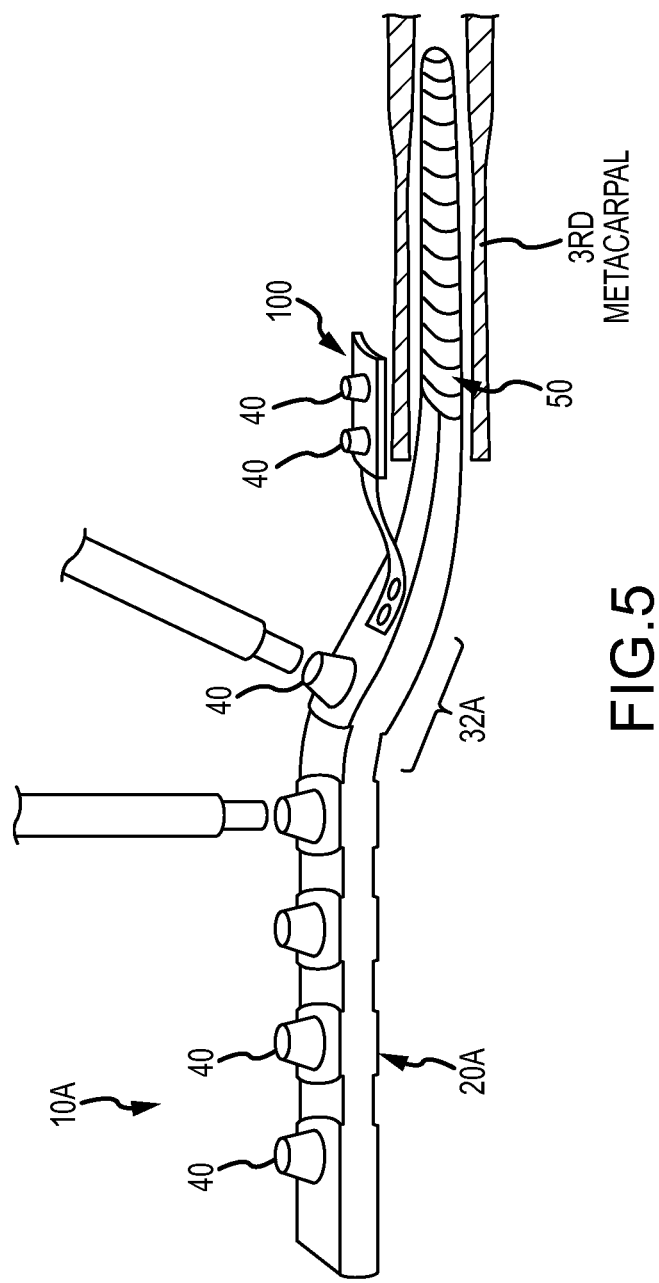
FIG. 5 is a side, perspective view of a device according to aspects of the invention with the second section inserted into the cannula of the third metacarpal and the third section attached to the top of the third metacarpal.

First section 20 is preferably an elongated plate having a length of 45 mm-75 mm, and most preferably about 60 mm, a thickness of between 3 and 4 mm, and most preferably about 3.5 mm, and a width of 9-15 mm, and most preferably about 11 mm. First section 20 includes a first end 22, apertures 24, a top surface 26 and a bottom surface 28. Apertures 24 pass from top surface 26 through bottom surface 28 to enable bone screws (which means any device suitable to connect first section 20 to one or more bones in the forearm and/or wrist) 30, which are shown in FIGS. 6 and 7, to pass through and connect to a bone, such as the radius and/or a carpal bone. Screws 30 are preferably standard bone screws known in the art. As shown in FIG. 5, drill guides 40 may be associated with each aperture 26 to assist in quickly positioning and drilling screws 30.

As shown in FIG. 7, openings 24 may be formed as compression slots 24A capable of accepting either one or two screws 30. If formed as compression slots, the ends of each slot farthest from the hand are sloped inward so that a screw 30 positioned at that location will push against the sloped surface and press section 20A away from the hand to create compression along the bone. If the slot 24A is long enough another screw 30 may be positioned, for example, in slotted retainer 24B, to secure device 10.

First section 20 also preferably includes a bended portion, or bend, 32. Bend 32 is at a preferred angle of about 10°-20°, is positioned at the wrist and marks the transition from the portion of device 10 on the forearm to the portion on the top of the hand. In a preferred embodiment, the bend has a drop D of between 0.5 and 1.5, and most preferably about 1.0 cm, and a length of between 15 and 25 mm, and most preferably 20 mm. Alternatively, first section 20 may be straight.

There are preferably three or more apertures 24 (or 24A) on first section 20, and most preferably five with one located at about the center of the wrist.

Second section 50 is either connected to or (most preferably) integrally formed with first section 20. As shown, after or during the bend 32, device 10 narrows and conforms in shape to form second end 50, although it could conform in shape to form second end 50 at any suitable location, whether or not device 10 has a bend 32. In this embodiment, second end 50 has an end 52 and a cylindrical body 54. Depending on the overall shape of device 10, second section 50 may extend upward at a 10°-20° angle, and most preferably about 15°, from the position at which it meets first portion 20, or extend straight from that position, or extend at any suitable angle. As shown, second section 50 is between 30 and 50 mm, and most preferably about 40 mm in length. The portion that extends into the cannula of the third metacarpal is preferably 3-4 mm, and most preferably about 3.5 mm in diameter. Second section 50 may include either longitudinal ribs, latitudinal ribs, or both.

An optional third section 100 is an anti-rotational section that helps prevent device 10 from rotating. Preferably third section 100 is a separate piece attached to device 10 immediately after bend 32 or at any suitable location. Third section 100 extends upward and outward so that it extends generally above second section 50. It has an attachment portion 102 with one or more screw holes 104 (shown in FIG. 7) that receive fasteners 106 to attach it to device 100. Upward and outward extending portion 108 has an extension 108A that includes one or more screw holes 110. Fasteners 112 (which are preferably bone screws) can pass through screw holes 110 and connect to the top of the third metacarpal bone to help prevent device 10 from rotating.

Optionally, second portion 50 has one or more receiving apertures 60 (shown in FIG. 7) that are positioned in the cannula of the third metacarpal when the second portion 50 is properly positioned in the hand. Each of the receiving apertures 60 is configured to receive the end of a fastener that is fastened to both the top bone of the third metacarpal and a receiving aperture 60 of the second portion 50 to further help prevent rotation. Another option to provide an anti-rotational structure is to eliminate the third section 100 and just insert one or more fasteners into the top bone of the third metacarpal and have each of the fasteners received in a receiving aperture 60 of the second section, as described above.

Figure 3:
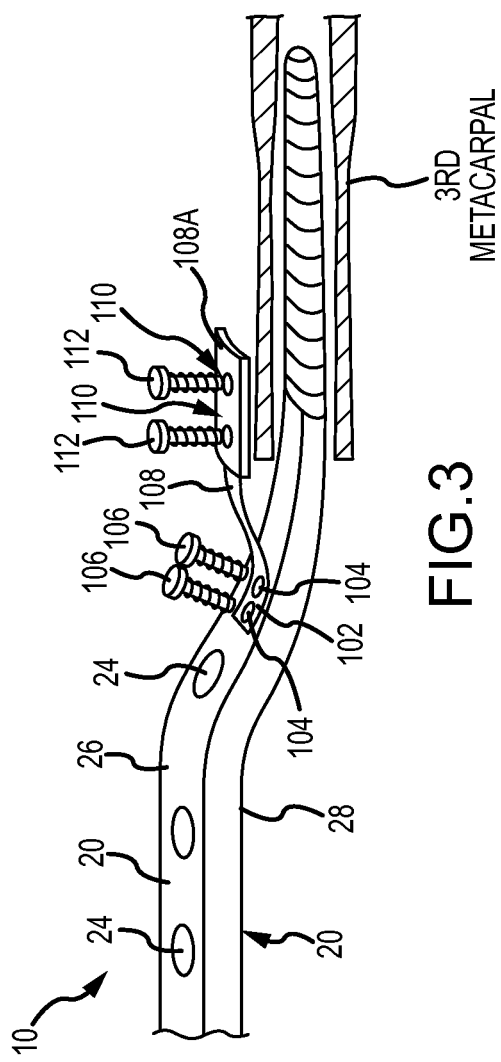
FIG. 3 is a perspective, side view of the device of FIG. 1 with the second section inserted in the cannula of the third metacarpal.
Figure 4:
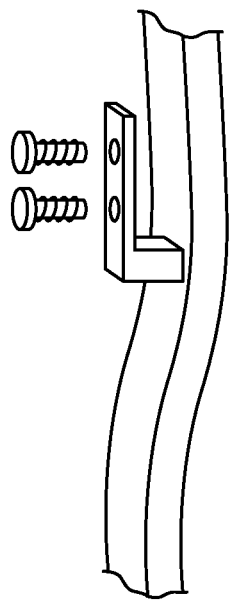
FIG. 4 is a partial, side perspective view of a device according to aspects of the invention.

FIG. 4 shows a third section 100A with a right angle, instead of the generally S-sloped, shape of third section 100. A third section according to the invention could be integrally formed with device 10 instead of being connected thereto.

In use, an appropriate incision is made preferably lengthwise along the hand, across the wrist and along part of the forearm so that device 10 may be received under the skin. The wrist is then flexed downward and second section 50 is pressed into the cannula of the third metacarpal bone. If the third section 100 is used, and if not integrally formed with device 10, it will preferably have already been connected to device 10 prior to the placement of second section 50 into the third metacarpal bone. Third section 100 (if used) is secured to the top of the third metacarpal bone by positing screws 106 through the screw holes and securing them to the top of the third metacarpal bone, as previously described. Alternatively, screws 106 may also be received into receiving apertures formed in second portion 50 that are positioned inside the third metacarpal bone. Or, no third section 100 is used and one or more screws are positioned through the top of the third metacarpal bone and into one or more receiving apertures of the second portion 50 to help prevent rotation.

Then wrist is straightened and section 20 is positioned o the forearm and wrist. Screws 30 are then placed through the apertures 24 into the radius and/or one or more carpal bones to secure device 10.

Some specific examples of the invention are as follows:
1. A device for fusion of the wrist, the device comprising:
   (a) a first substantially rigid section configured to be positioned under the skin of the forearm and wrist, and to be secured to at least one or more bones in the forearm; and
   (b) a second section connected to or integrally formed with the first section, the second section configured to be received in the cannula of the third metacarpal bone.
2. The device of example 1 wherein the first section is an elongated plate.
3. The device of example 1 or example 2 wherein the first section has a downward bend between the wrist and the hand.
4. The device of example 3 wherein the downward bend is at an angle of 10°-20°.
5. The device of any of examples 1-4 wherein the first section has apertures that permit screws to pass through.
6. The device of any of examples 1-5 that further includes drill guides associated with each aperture in the first section.
7. The device of any of examples 1-6 wherein the first section is between 3.0 and 4.0 mm thick.
8. The device of any of examples 1-3 or 5-7 wherein the bend has a drop of between 0.5 and 1.5 cm and extends along the device for a length between 15 and 25 mm.
9. The device of any of examples 1-8 wherein the first section is between 9 mm and 15 mm wide.
10. The device of any of examples 1-9 wherein the first section has three or more apertures.
11. The device of any of examples 1-10 wherein the first section has five apertures.
12. The device of any of examples 5, 10 or 11 that has an aperture above the wrist to enable a screw to be inserted into a bone at the wrist.
13. The device of any of examples 1 and 2 wherein the second section is integrally formed with the first section.
14. The device of any of examples 1-13 wherein the second section extends at an upward angle of between 10° and 20° from the point at where it meets the first section.
15. The device of any of examples 1-13 wherein the second section extends at an upward angle of between 15° from the point at where it meets the first section.
16. The device of any of examples 1 and 15 wherein the second section is between 30 and 50 mm in length.

17. The device of any of examples 1 and 15 wherein the second section is 40 mm in length.
18. The device of any of examples 1-17 wherein the portion of the second section that extends into the cannula of the third metacarpal bone is between 2 mm and 4 mm in diameter.
19. The device of any of examples 1-17 wherein the portion of the second section that extends into the cannula of the third metacarpal bone is 3 mm in diameter.
20. The device of any of examples 1-19 that further includes an anti-rotational section.
21. The device of example 20 wherein the anti-rotational section is connected to the first section.
22. The device of any of examples 3, 4 or 8 that further includes an anti-rotational section connected to the device past the bend and on the part of the device which is to be positioned on the hand.
23. The device of any of examples 20-22 wherein the anti-rotational section is connected to the device by screws.
24. The device of any of examples 20-23 wherein the anti-rotational section extends upward and outward from the device and extends above the second section so that it can be connected to the top of the third metacarpal bone.
25. The device of any of examples 20-24 wherein the anti-rotational device includes one or more screw holes to allow a screw to pass through it and connect to the top of the third metacarpal bone.
26. The device of example 1 that includes an anti-rotational device integrally formed therewith.
27. The device of any of examples 1-26 that is comprised of stainless steel.
28. The device of any of examples 1-27 wherein the first section has a length of 45-75 mm.
29. The device of any of examples wherein the first section has a length of 60 mm.
30. The device of any of examples 1-29 wherein the device has a length of 105-135 mm.
31. The device of any of examples 1-29 that has a length of 120 mm.
32. The device of example 1 or example 2 wherein the first section is straight.
33. The device of any of examples 1-2 wherein the second section extends straight from the point at which it meets the first section.
34. The device of example 26 wherein the anti-rotational section extends above and outward from the device and extends above the second section so that it can be connected to the top of the third metacarpal bone.
35. The device of example 26 or example 34 wherein the anti-rotational device includes one or more screw holes to allow a screw to pass through it and connect to the top of the third metacarpal bone.
36. The device of any of examples 1-35 wherein the second section has one or more receiving apertures that is positioned in the cannula of the third metacarpal when the second section is properly positioned in the hand, each of the one or more receiving apertures for receiving a fastener positioned through the top of the third metacarpal bone in order to secure the top of the third metacarpal bone to the second portion, in order to help prevent rotation of the device.
37. The device of example 36 wherein each of the fasteners is a screw.
38. The device of example 36 wherein each of the one or more receiving apertures is threaded to threadingly receive a screw.

Having thus described some embodiments of the invention, other variations and embodiments that do not depart from the spirit of the invention will become apparent to those skilled in the art. The scope of the present invention is thus not limited to any particular embodiment, but is instead set forth in the appended claims and the legal equivalents thereof. Unless expressly stated in the written description or claims, the steps of any method recited in the claims may be performed in any order capable of yielding the desired result.

What is claimed is:

1. A wrist fusion implant having a length along an implant longitudinal axis, the implant comprising:
   a distal intramedullary metacarpal portion that has a thickness, a length, a width, and a first longitudinal axis along the length of the distal intramedullary metacarpal portion;
   a proximal dorsal radial plate portion that has a thickness, a length, and a second longitudinal axis along the length of the proximal dorsal radial plate portion, the proximal dorsal radial plate portion comprising a bone-facing surface that is configured to overlay a dorsal aspect of a radius and an opposing surface, wherein a plurality of apertures extend from the bone-facing surface to the opposing surface; and
   an intermediate carpal portion that links the distal intramedullary metacarpal portion with the proximal dorsal radial plate portion along the implant longitudinal axis, the intermediate carpal portion defining a third longitudinal axis along a length of the intermediate carpal portion, the third longitudinal axis at a first angle with the second longitudinal,
   wherein the distal intramedullary metacarpal portion is pre-shaped such that, when at rest, the first longitudinal axis extends at a second angle relative to the second longitudinal axis, a distal end of the distal intramedullary metacarpal portion extending toward the second longitudinal axis and spaced apart from the second longitudinal axis.

2. A wrist fusion implant as set forth in claim 1, wherein the intermediate carpal portion is at from 10° to 20° relative to the proximal dorsal radial plate portion.

3. A wrist fusion implant as set forth in claim 1, wherein the distal intramedullary metacarpal portion has a tapered end.

4. A wrist fusion implant as set forth in claim 3, wherein the distal intramedullary metacarpal portion has a cross-section which is circular.

5. A wrist fusion implant as set forth in claim 1, wherein the distal intramedullary metacarpal portion further includes a non-rotational feature.

6. A wrist fusion implant as set forth in claim 5, wherein the distal intramedullary metacarpal portion further includes one or more apertures and the non-rotational feature comprises one or more fasteners that are received in the one or more apertures.

7. A wrist fusion implant as set forth in claim 1, wherein the plurality of the apertures of the proximal dorsal radial portion comprise a compression slot.

8. A wrist fusion implant as set forth in claim 1, wherein the proximal dorsal radial plate portion has a width of 9 to 15 mm.

9. A wrist fusion implant as set forth in claim 1, further comprising an anti-rotational section extending from a location on the distal intramedullary metacarpal portion, the intermediate carpal portion, or the proximal dorsal radial plate portion and extending over the distal intramedullary metacarpal portion along the length of the distal intramedullary metacarpal portion.

10. A wrist fusion implant as set forth in claim 9, wherein the anti-rotational section comprises a plurality of openings configured to receive fasteners that are configured to connect the implant to a metacarpal bone via an outer surface of the metacarpal bone.

11. A wrist fusion implant as set forth in claim 1, wherein the distal intramedullary metacarpal portion comprises a plurality of ribs that are spaced apart along the length of the distal intramedullary metacarpal portion.

12. A wrist fusion implant as set forth in claim 1, wherein the distal intramedullary metacarpal portion extends upward at an angle of from 10° to 20° from a position where the distal intramedullary metacarpal portion meets the intermediate carpal portion.

13. A wrist fusion implant system comprising:
an implant; and
at least one fixator;
wherein the implant comprises a stepped profile along an implant longitudinal axis with a first section and a second section,
the second section comprising a distal intramedullary metacarpal spike portion configured to reside within at least a portion of a metacarpal bone, the second section having a cross-section that is rounded and defining a thickness, a length, a width, and a first longitudinal axis along the length of the second section, the first section joined along the implant longitudinal axis to the second section;
the first section comprising:
a proximal plate portion off-set from the distal intramedullary metacarpal spike portion, the proximal plate portion having a length, a thickness, and a second longitudinal axis along the length of the proximal plate portion, the proximal plate portion comprising a bone-facing surface that is configured to overlay and be connected to a cortical aspect of a radius and an opposing surface, wherein a plurality of apertures extend from the bone-facing surface to the opposing surface such that each aperture is capable of receiving the at least one fixator to connect the proximal plate portion to the radius, and
an intermediate carpal portion that extends obliquely relative to the implant longitudinal axis to link the distal intramedullary metacarpal spike portion with the proximal plate portion along the implant longitudinal axis,
wherein the distal intramedullary metacarpal spike portion is pre-shaped such that, when at rest, the first longitudinal axis extends at an angle relative to the second longitudinal, a distal end of the distal intramedullary metacarpal spike portion extending toward the second longitudinal axis and spaced apart from the second longitudinal axis.

14. A wrist fusion implant system as set forth in claim 13, wherein the proximal plate portion has a width of 9 to 15 mm.

15. A wrist fusion implant system as set forth in claim 13, wherein the intermediate carpal portion is at from 10° to 20° relative to the proximal plate portion.

16. A wrist fusion implant system as set forth in claim 13, comprising a third section that comprises an anti-rotational section extending from a location of the first or second section and extending over the second section along the length of the second section.

17. A wrist fusion implant system as set forth in claim 16, wherein the third section comprises a plurality of openings, the at least one fixator configured to be received in at least one of the plurality of openings to couple the implant to the metacarpal bone via an outer surface of the metacarpal bone.

18. A wrist fusion implant system as set forth in claim 13, wherein the second section comprises a plurality of ribs.

19. A wrist fusion implant as set forth in claim 13, wherein the second section extends upward at an angle of from 10° to 20° from a position where the second section meets the first section.

* * * * *